United States Patent
Waugh et al.

(10) Patent No.: US 7,631,541 B2
(45) Date of Patent: Dec. 15, 2009

(54) METHOD OF MEASURING A SET CEMENT DENSITY AND SETTLING PROPERTIES

(75) Inventors: Bryan Waugh, Comanche, OK (US); Christopher Gordon, Duncan, OK (US)

(73) Assignee: Halliburton Energy Services, Inc., Duncan, OK (US)

( * ) Notice: Subject to any disclaimer, the term of this patent is extended or adjusted under 35 U.S.C. 154(b) by 227 days.

(21) Appl. No.: 11/868,708

(22) Filed: Oct. 8, 2007

(65) Prior Publication Data

US 2009/0090180 A1 Apr. 9, 2009

(51) Int. Cl.
*G01N 9/00* (2006.01)
(52) U.S. Cl. ...................................... 73/32 R
(58) Field of Classification Search .................. 73/32 R
See application file for complete search history.

(56) References Cited

U.S. PATENT DOCUMENTS

| | | | | |
|---|---|---|---|---|
| 4,941,536 | A * | 7/1990 | Brothers et al. | 166/293 |
| 6,729,405 | B2 * | 5/2004 | DiLullo et al. | 166/292 |
| 7,530,396 | B1 * | 5/2009 | Reddy et al. | 166/293 |
| 2007/0194476 | A1 * | 8/2007 | Ramsey | 264/41 |

* cited by examiner

*Primary Examiner*—John Fitzgerald
(74) *Attorney, Agent, or Firm*—John W. Wustenberg; Baker Botts, LLP

(57) ABSTRACT

An improved method for measuring the density and settling properties of cement slurries. The cement slurry is stirred in a consistometer and heated to a predetermined temperature. The stirring of the cement slurry is then halted and the cement slurry is cooled. The cement slurry is then removed from the consistometer.

20 Claims, 3 Drawing Sheets

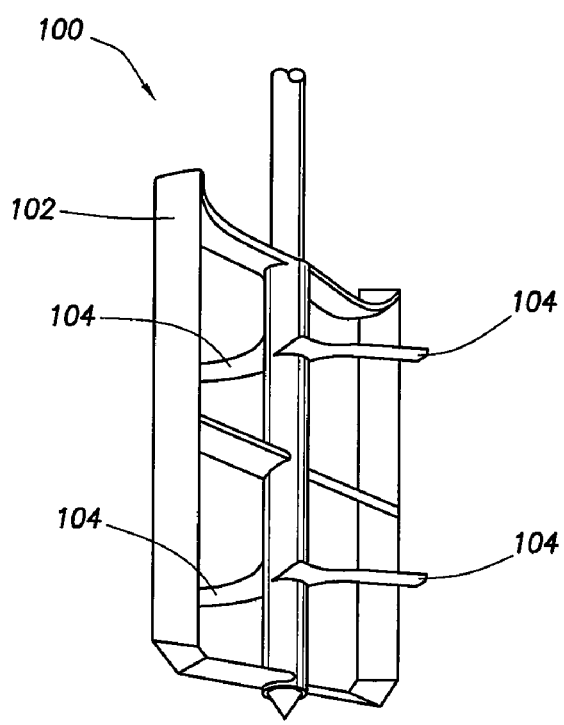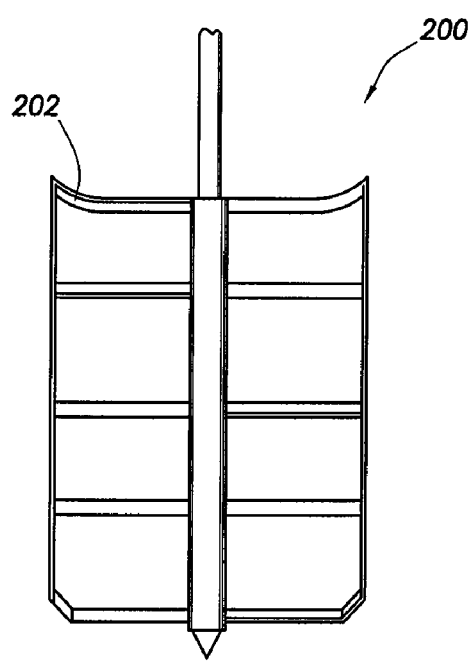
FIG.1
(PRIOR ART)
FIG.2

METHOD OF MEASURING A SET CEMENT DENSITY AND SETTLING PROPERTIES

BACKGROUND OF THE INVENTION

The present invention primarily relates to subterranean cementing operations. More particularly, the present invention relates to an improved method for measuring the density and settling properties of cement slurries.

Hydraulic cement compositions are frequently utilized in subterranean well completion and remedial operations. In cementing operations carried out in oil, gas and other wells, a hydraulic cement and various additives are mixed with sufficient water to form a pumpable slurry, and the slurry is pumped into a subterranean zone to be cemented.

For instance, in primary cementing operations hydraulic cement compositions are used to cement strings of pipes such as casings and liners in well bores. In performing primary cementing, a hydraulic cement composition is pumped into the annular space between the walls of a well bore and the exterior surfaces of a pipe string disposed therein. The cement composition is then permitted to set in the annular space. Once hardened, the cement composition forms an annular sheath of substantially impermeable cement which supports and positions the pipe string in the well bore and bonds the exterior surfaces of the pipe string to the walls of the well bore. Hydraulic cement compositions are also used in remedial cementing operations such as plugging highly permeable zones or fractures in well bores, plugging cracks or holes in pipe strings and the like.

It is desirable to create a set cement where the density of the slurry remains consistent from the top to the bottom of the cemented formation. However, solid segregation in the cement slurry causes the fluid portion to migrate upward through the slurry after it is placed in the well bore creating an uncemented area in the annulus. The movement of the fluid portion reduces the density consistency of the cemented portion and the existence of the uncemented area makes the cemented portion unstable. The formation of the free fluid is particularly harmful in deviated or horizontal wells because it can collect along the high side of the annulus forming a channel which can contribute to zonal communication or gas migration. This concern is magnified because the driving force for segregation and separation of the slurry is much more prevalent under deviated conditions. Even in vertical wells, pockets of free fluid located near a corrosive water zone can eventually result in casing leaks. Consequently, the capability of a cement slurry to maintain good suspension properties under downhole conditions is critical.

The amount of water that will separate from a cement slurry during the settling process is referred to as the free water. Historically, the free water amount for a particular slurry has been determined utilizing a standard American Petroleum Institute (API) test well known in the art. During this API test, a 9.4 inch sample of the cement slurry is placed into a 1.375 inch diameter column. As the cement slurry sets, a small amount of water separates from the cement slurry and accumulates on the top of the column. The amount of water accumulated is measured after two hours and is the free water for the particular slurry sample being tested. An excessive amount of free water is a symptom of a poor cement and a poor cement slurry.

A major drawback of the API free water test is that the test is usually carried out at room temperature and atmospheric pressure, rather than at the actual temperature and pressures encountered in the well bore environment. Moreover, the free water test cannot be used at temperatures exceeding 190 degrees Fahrenheit. The suspension properties of a cement slurry tend to reduce at higher temperatures. Because the rate at which a cement slurry cures is dependent upon the surrounding temperature and pressure and the free water test is not conducted under conditions existing during actual use, the free water test does not provide an accurate result.

The BP Settling Test was developed by BP International Ltd as an alternative means to perform relative measurements of cement formulation stability at elevated temperatures and pressures. Generally, in the BP Settling Test the cement slurry is allowed to set hard, permitting free water, unconsolidated solids, and the density profile of the set solids to be distinguished and measured. Specifically, a cement slurry is prepared and heated to the Bottom Hole Circulating Temperature (BHCT) in a pressurized consistometer. The BHCT represents the temperature of a circulating fluid at the bottom of the wellbore after several hours of circulation. The slurry is then cooled and transferred into a settling tube where it is allowed to cure at BHCT. The stability of the slurry is determined once the cement has set. First, the height of the set column of cement is measured and compared with the original height to determine the amount of free water and unconsolidated solids that result from slurry segregation. Next, the settling tube is broken and the cement column is cut into different sections. The density along the cement column is then measured by measuring the bulk volume of each section using the Archimedes Principle.

The BP Settling Test has several disadvantages. First, the cement slurry is subject to aeration when being transferred to the settling tube. This aeration of the cement slurry should be minimized during mixing as any entrained air in the cement slurry will be compressed when the cement is pressurized in the curing chamber causing the cement column to shrink. The shrinkage of the cement column due to compression of air will cause errors in the measurement of the slurry stability. To prevent this false indication of settling the slurry should be placed under a partial vacuum before it is placed in the settling tube. This process is expensive and time consuming.

Another shortcoming of the BP Settling Test is that with today's increasing temperatures and pressures of cementing, the BP Settling Test has inherent risks and problems that could lead to false readings of a cement density. Specifically, in the BP Settling Test the sample is heated to the BHCT, removed from the consistometer and cooled down before being transferred to the settling tubes and reheated to the BHCT. These steps are time consuming and hazardous. Moreover, the temperature reduction of the slurry is often accompanied by a viscosification of the slurry as it cools. This viscosification alters the slurry properties and reduces the test's accuracy as there is no such cooling in real downhole conditions.

Yet another disadvantage of the BP Settling test is that once the settling tube is broken, shards of glass have to be carefully removed from the slurry surface before further measurements can be obtained. This process is time consuming and gives rise to safety concerns.

SUMMARY

The present invention primarily relates to subterranean cementing operations. More particularly, the present invention relates to an improved method for measuring the density and settling properties of cement slurries.

In one embodiment the present invention is directed to a method for analyzing a cement slurry comprising the steps of: placing a cement slurry in a consistometer having a paddle, heating the cement slurry; allowing the cement slurry to set;

cooling the cement slurry; removing the paddle; cutting off a set cement slurry sample from the paddle; and analyzing the sample.

In another embodiment, the present invention is directed to a method of analyzing a cement slurry comprising the steps of: stirring a cement slurry in a consistometer; heating the cement slurry to a predetermined temperature; halting the stirring of the cement slurry; cooling the cement slurry; and removing the cement slurry from the consistometer.

In yet another embodiment, the present invention is directed to a method of analyzing a cement slurry comprising the steps of: stirring a cement slurry with a generally planar paddle in a consistometer; heating the cement slurry to a first temperature; halting the stirring of the cement slurry; changing temperature of the cement slurry to a second temperature; cooling the cement slurry; and removing the cement slurry from the consistometer. The cement slurry sets on the planar paddle.

The features and advantages of the present invention will be apparent to those skilled in the art from the description of the preferred embodiments which follows when taken in conjunction with the accompanying drawings. While numerous changes may be made by those skilled in the art, such changes are within the spirit of the invention.

BRIEF DESCRIPTION OF THE DRAWINGS

These drawings illustrate certain aspects of some of the embodiments of the present invention, and should not be used to limit or define the invention.

FIG. 1 illustrates a consistometer paddle in accordance with the prior art.

FIG. 2 illustrates a consistometer paddle in accordance with an embodiment of the present invention.

DESCRIPTION OF PREFERRED EMBODIMENTS

Figure 3:
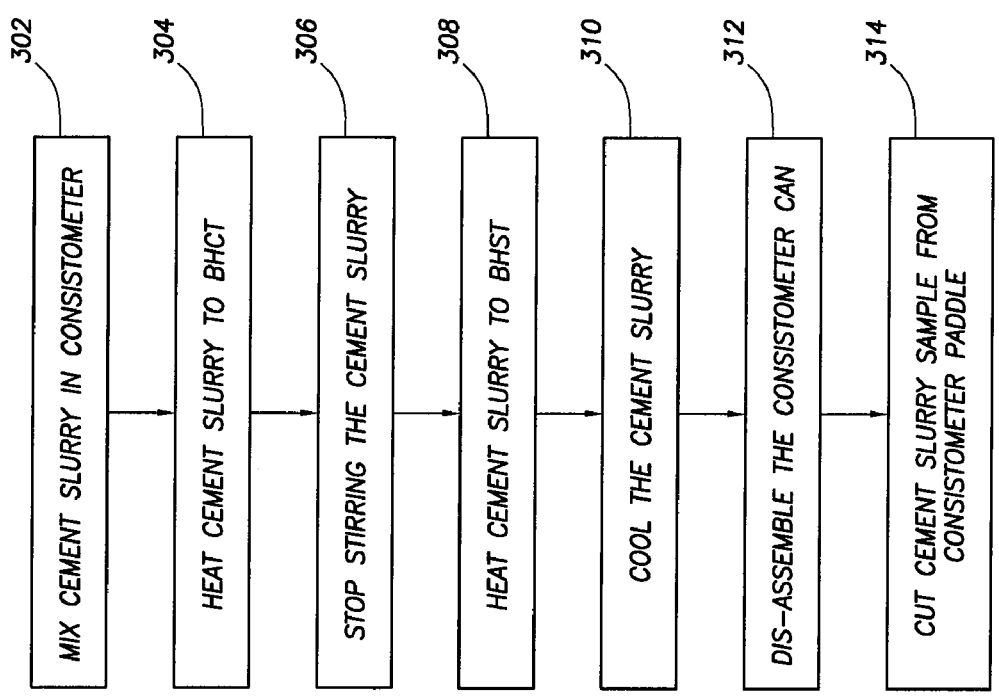
FIG. 3 is a flow diagram of the steps for a settling test in accordance with an embodiment of the present invention.

The present invention primarily relates to subterranean cementing operations. More particularly, the present invention relates to an improved method for measuring the density and settling properties of cement slurries.

Turning now to FIG. 1, a consistometer paddle 100 in accordance with the prior art is depicted. The paddle 100 consists of a partitioned frame 102 with protruding portions 104. The cement slurry is mixed in the consistometer can through rotations of the paddle 100. As the paddle 100 rotates, the partitioned frame 102 and the protruding portions 104 mix the slurry. FIG. 2 depicts a paddle 200 used in a consistometer for carrying out a settling test in accordance with an embodiment of the present invention. The paddle 200 includes a planar partitioned frame 202 and does not have any portions protruding from the plain of the frame.

FIG. 3 illustrates a flow diagram of the steps for conducting a settling test in accordance with an embodiment of the present invention. At step 302, the cement slurry is placed in a consistometer. The sample is placed in the consistometer's can. The consistometer also includes an improved paddle 200. The consistometer motor is turned on and the paddle rotates, mixing the cement slurry in the consistometer can. Then, at step 304, the cement slurry is brought up to the Bottom Hole Circulating Temperature ("BHCT") and Bottom Hole Pressure ("BHP") while being stirred by the improved paddle 200. In an exemplary embodiment a High Pressure High Temperature ("HPHT") program is used to increase the pressure and temperature of the cement slurry to the BHCT and BHP. In one embodiment the cement slurry's temperature and pressure reaches the BHCT and BHP in a pre-specified time representing the time it would take to get all the cement slurry placed in position for a particular job, or the "job time"

The consistometer motor is then turned off at step 306. The movement of the paddle 200 stops and the cement slurry is no longer being stirred. Next, at step 308 the HPHT program heats the cement slurry up to the Bottom Hole Static Temperature ("BHST"). The BHST represents the downhole temperature under static conditions and after sufficient time has elapsed to negate any effect of the circulating fluid. The BHST is typically higher than the BHCT. The BHST for a particular job may be estimated in a variety of ways. For example, tables, charts and computer routines may be used to predict the BHST as a function of a number different factors such as the job depth or the geographic area where the job is to be performed.

Turning off the motor and heating up the cement slurry to the BHST closely simulates the actual conditions under ground after the cement has been put in place. Specifically, this step simulates the stage where the cement is put in place on the field and undergoes an increase in temperature as it becomes static. In one embodiment, the BHST is achieved in a minimum of 4 hours. The slurry is maintained at the BHST for a predetermined period of time. In one exemplary embodiment, the slurry is maintained at the BHST for a period of at least 12 hours from the time the motor is turned off. Once the cement slurry is retained at the BHST for the pre-specified time and begins to set, at step 310, the HPHT program cools down and depressurized the consistometer can over a set amount of time.

Figure 4:
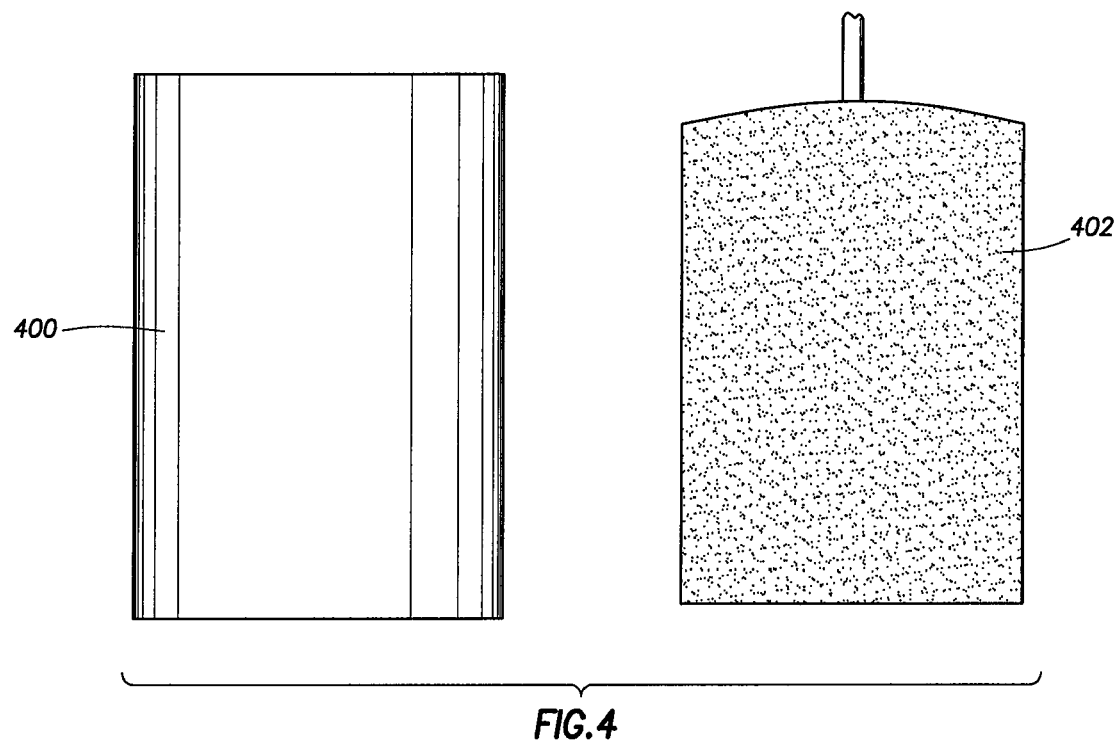
FIG. 4 depicts the paddle of FIG. 2 removed from the consistometer can with the cement slurry set on the paddle.

At step 312, the consistometer can is disassembled and the set slurry which is now hardened around the consistometer paddle 200 is removed from the consistometer can. FIG. 4 shows the paddle 200 removed from the consistometer can 404 with the cement slurry 402 set on the paddle 200. As depicted in FIG. 4, the set cement slurry 402 forms a cylindrical body around the paddle 200. As would be appreciated by those of ordinary skill in the art, with the benefit of this disclosure, the set cement may take on other shapes depending on the shape of the consistometer can.

Returning now to FIG. 3, a cement slurry sample is cut off from the paddle 200 at step 314. The improved paddle design provides for an easy removal of the hardened cement sample. Removal of the cement slurry sample from the paddle was not possible in the prior art, mainly because of the protruding portions 104 of the paddle 100. Specifically, an attempt to cut off the cement sample from a paddle in accordance with the prior art would damage the paddle itself.

In contrast, in an embodiment of the present invention a rock saw may be used to cut off the set cement from the improved paddle 200. Because the improved paddle does not have any portions protruding from its planar frame, the hardened cement sample can be easily cut off from the paddle itself. Specifically, the cement sample may be cut off from the paddle 200 by cutting parallel to the paddle's planar frame on each side of the frame. The cement sample is then turned perpendicular and cut along its horizontal axis into three parts having substantially equal lengths. These parts represent the top, the middle and the bottom of the cement sample. The characteristics of the cement samples obtained may then be studied. In one embodiment, the density of the samples may be measured using the Archimedes principle which is well known in the art.

The setting time for cement is temperature dependent. As a result, the accuracy of any analysis of the cement slurry is largely dependent upon how closely the test temperature resembles the actual temperature conditions on the field where the slurry is to be used. As discussed above, the testing method of the present invention maintains the cement slurry under the predetermined temperature and pressure throughout the test, therefore simulating what the slurry is actually subjected to in downhole conditions. Specifically, the sample need not be cooled down and removed from the HPHT machine in order to be transferred to the settling tubes and reheated. Therefore, the new method does not involve viscosification of the slurry in the middle of the test due to cooling and transfer of the slurry at room temperature. The elimination of this step improves the test's accuracy, saves time and reduces the hazards associated with removing the glass shards from the sample once the settling tube is broken.

Additionally, the testing method of the present invention reduces the risk of oil contamination of the cement slurry by eliminating the open-ended glass tubes used in the BP Settling test.

To facilitate a better understanding of the present invention, the following examples of certain aspects of some embodiments are given. In no way should the following examples be read to limit, or define, the scope of the invention.

EXAMPLES

Tables 1.1 and 1.2 depict the result of analyzing two different samples. Table 1.1 depicts the results of analyzing a "stable" sample. In contrast, table 1.2 depicts the results from analyzing an unstable sample. Each sample was analyzed with both the BP Settling Test and the method in accordance with an embodiment of the present invention. As demonstrated in the tables, the new method yields more accurate results.

TABLE 1.1

Slurry with good suspension - Actual pressurized balance weight - 18.00 ppg

| 18 ppg Slurry - Known to be stable | New Method | BP Settling Test |
| --- | --- | --- |
| Top Sample | 18.00 ppg | 18.03 ppg |
| Middle Sample | 18.06 ppg | 18.02 ppg |
| Bottom Sample | 18.19 ppg | 18.21 ppg |

TABLE 1.2

Slurry with bad suspension - Actual pressurized balance weight - 17.95 ppg

| 17.95 ppg Slurry - Known to be unstable | New Method | BP Settling Test |
| --- | --- | --- |
| Top Sample | 17.77 ppg | 17.75 ppg |
| Middle Sample | 18.48 ppg | 17.94 ppg |
| Bottom Sample | 19.28 ppg | 18.77 ppg |

What is claimed is:

1. A method for analyzing a cement slurry comprising the steps of:
    placing a cement slurry in a consistometer having a paddle;
    heating the cement slurry;
    allowing the cement slurry to set;
    cooling the cement slurry;
    removing the paddle;
    cutting off a set cement slurry sample from the paddle; and
    analyzing the sample.

2. The method of claim 1, further comprising the step of cutting the set cement slurry sample into a plurality of smaller sections corresponding to a top portion sample, a middle portion sample and a bottom portion sample.

3. The method of claim 1, wherein the step of heating the cement slurry comprises heating the cement slurry to a Bottom Hole Circulating Temperature.

4. The method of claim 1, wherein the paddle comprises a generally planar frame.

5. The method of claim 4, wherein the step of cutting off the set cement slurry sample from the paddle comprises cutting the set cement slurry parallel to the generally planar frame.

6. The method of claim 1, wherein the step of heating the cement slurry comprises:
    heating the cement slurry at a Bottom Hole Circulating Temperature during a first time period; and
    heating the cement slurry at a Bottom Hole Static Temperature during a second time period;
    wherein the cement slurry is stirred during the first time period and not stirred during the second time period.

7. The method of claim 6, wherein the first time period represents a job time.

8. The method of claim 6, wherein the second time period is at least about 12 hours.

9. The method of claim 6, wherein temperature of the cement slurry changes from the Bottom Hole Circulating Temperature to the Bottom Hole Static Temperature in a time period of at least 4 hours.

10. A method of analyzing a cement slurry comprising the steps of:
    stirring a cement slurry in a consistometer;
    heating the cement slurry to a predetermined temperature;
    halting the stirring of the cement slurry;
    cooling the cement slurry;
    removing the cement slurry from the consistometer; and
    analyzing the cement slurry.

11. The method of claim 10, wherein the predetermined temperature is a Bottom Hole Circulating Temperature.

12. The method of claim 10, wherein stirring the cement sample is carried out by a planar paddle.

13. A method of analyzing a cement slurry comprising the steps of:
    stirring a cement slurry with a generally planar paddle in a consistometer;
    heating the cement slurry to a first temperature;
    halting the stirring of the cement slurry;
    changing temperature of the cement slurry to a second temperature;
    cooling the cement slurry;
    removing the cement slurry from the consistometer; and
    analyzing the cement slurry,
    wherein the cement slurry sets on the planar paddle.

14. The method of claim 13, wherein the first temperature is a Bottom Hole Circulating Temperature.

15. The method of claim 13, wherein the second temperature is a Bottom Hole Static Temperature.

16. The method of claim 13, wherein the cement slurry is stirred for a period of time representing a job time.

17. The method of claim 13, wherein the cement slurry is maintained at the second temperature for at least 12 hours.

18. The method of claim 13, further comprising cutting off a cement slurry sample from the cement slurry set on the paddle.

19. The method of claim 18, further comprising cutting the cement slurry sample into three parts representing a top sample, a middle sample and a bottom sample.

20. The method of claim 19, further comprising analyzing a settling property of the top sample, the middle sample and the bottom sample.

* * * * *